US012589070B2

(12) United States Patent
Criere et al.

(10) Patent No.: US 12,589,070 B2
(45) Date of Patent: Mar. 31, 2026

(54) LOW-DOSAGE ORODISPERSIBLE OPIOID TABLET AND METHOD FOR PREPARING SAME

(71) Applicant: ETHYPHARM, Saint-Cloud (FR)

(72) Inventors: Bruno Criere, Gravigny (FR); Jack Zerrouk, Rouen (FR)

(73) Assignee: ETHYPHARM, Saint-Cloud (FR)

( * ) Notice: Subject to any disclaimer, the term of this patent is extended or adjusted under 35 U.S.C. 154(b) by 757 days.

(21) Appl. No.: 17/634,684

(22) PCT Filed: Aug. 13, 2020

(86) PCT No.: PCT/FR2020/051464
§ 371 (c)(1),
(2) Date: Feb. 11, 2022

(87) PCT Pub. No.: WO2021/028640
PCT Pub. Date: Feb. 18, 2021

(65) Prior Publication Data
US 2022/0296507 A1 Sep. 22, 2022

(30) Foreign Application Priority Data

Aug. 13, 2019 (FR) ................................. FR1909185

(51) Int. Cl.
*A61K 9/00* (2006.01)
*A61K 9/20* (2006.01)
*A61K 31/485* (2006.01)
*A61P 25/04* (2006.01)

(52) U.S. Cl.
CPC .......... *A61K 9/0056* (2013.01); *A61K 9/2009* (2013.01); *A61K 9/2018* (2013.01); *A61K 9/2027* (2013.01); *A61K 9/2054* (2013.01); *A61K 9/2095* (2013.01); *A61K 31/485* (2013.01); *A61P 25/04* (2018.01)

(58) Field of Classification Search
CPC .. A61K 9/0056; A61K 9/2009; A61K 9/2018; A61K 9/2027; A61K 9/2054; A61K 9/2095; A61K 31/485; A61P 25/04
See application file for complete search history.

(56) References Cited

U.S. PATENT DOCUMENTS

| | | | | |
|---|---|---|---|---|
| 2003/0125543 A1* | 7/2003 | Obara | .................. | A61K 9/2054 |
| | | | | 536/89 |
| 2004/0265380 A1* | 12/2004 | Delmas | .................. | A61P 37/00 |
| | | | | 424/466 |
| 2005/0147666 A1* | 7/2005 | Ohta | ........................ | A61P 3/06 |
| | | | | 424/464 |
| 2006/0177508 A1* | 8/2006 | Chauveau | ............ | A61K 9/2081 |
| | | | | 514/165 |
| 2009/0169620 A1* | 7/2009 | Venkatesh | ............ | A61K 9/1635 |
| | | | | 424/464 |
| 2009/0311320 A1* | 12/2009 | Oury | .................... | A61K 9/0056 |
| | | | | 514/629 |
| 2012/0282335 A1* | 11/2012 | Venkatesh | ............ | A61K 9/2095 |
| | | | | 514/630 |
| 2013/0108703 A1* | 5/2013 | Venkatesh | .............. | A61K 31/53 |
| | | | | 424/490 |

FOREIGN PATENT DOCUMENTS

| | | | |
|---|---|---|---|
| CN | 1328446 A | 12/2001 |
| CN | 103860499 A | 6/2014 |
| CN | 103877047 A | 6/2014 |
| WO | 0006126 A1 | 2/2000 |
| WO | 0027357 A1 | 5/2000 |
| WO | 0078292 A1 | 12/2000 |
| WO | 0119336 A1 | 3/2001 |
| WO | 0180822 A2 | 11/2001 |
| WO | 2007141328 A1 | 12/2007 |
| WO | 2009086046 A1 | 7/2009 |

OTHER PUBLICATIONS

Pharm Tech "Selecting Superdisintegrants for Orally Disintegrating Tablet Formulations" (2006) (Year: 2006).*
Kimura "Effect of granule properties on rough mouth feel and palatability of orally disintegrating tablets" International Journal of Pharmaceutics 484 (2015) 156-162. (Year: 2015).*
Rajniak "Experimental study of wet granulation in fluidized bed: Impact of the binder properties on the granule morphology" International Journal of Pharmaceutics 334 (2007) 92-102 (Year: 2007).*
Office Action issued on Feb. 6, 2024, in corresponding Chinese Application No. 202080056910.5, 14 pages.
International Search Report (with English Translation) and Written Opinion (with Machine Translation) issued on Nov. 27, 2020; 16 pages.

* cited by examiner

*Primary Examiner* — Ali Soroush
*Assistant Examiner* — Rajan Pragani
(74) *Attorney, Agent, or Firm* — Maier & Maier, PLLC

(57) ABSTRACT

A low-dosage orodispersible opioid tablet including: 10 to 30% by weight of opioid granules, and 70% to 90% by weight of a mixture of compression excipients. The granules include 8 to 27% by weight of the opioid and 72% to 93% by weight of a mixture of diluent and binder. The mixture of compression excipients includes at least one disintegrating agent, one diluting agent, one lubricating agent, one permeabilising agent, and optionally a sweetener, a flavouring and/or a colouring, the ratio between the lubricating agent and the permeabilising agent being greater than or equal to 1, the quantity of lubricating agent being 1 to 2% by weight of the tablet, and the quantity of permeabilising agent being 0.5 to 5% by weight of the tablet. Also, the method for preparing same.

10 Claims, No Drawings

LOW-DOSAGE ORODISPERSIBLE OPIOID TABLET AND METHOD FOR PREPARING SAME

The present invention relates to a low-dosage, immediate release oral pharmaceutical form of opioid, in particular of morphine and its salts, and to the method for preparing the same.

FIELD

Opioids, and in particular morphine, are used for the treatment of moderate to severe pain. Morphine is also used for the treatment of chronic pain.

PRIOR ART

Background

Orodispersible tablets or ODTs represent a galenical form in full expansion, which has been developed a great deal over the past few years. Indeed, orodispersible tablets have many advantages and are particularly suitable for patients who have difficulty swallowing, for example children and the elderly. However, these populations are not the only ones to experience problems swallowing, since approximately 30% to 50% of the population is affected by this problem. Orodispersible tablets are also suitable for individuals who do not have easy access to water, in particular during journeys. One other advantage of said tablets is that they allow practical and discrete use.

Thus, even though orodispersible tablets remain quite a widespread form that are liked by patients, in particular for their practical and rapid use, a study carried out by the applicant has shown that the taste and the feeling of a tablet in the mouth appear to be very important parameters for patients, and therefore a bad taste and/or unpleasant feeling in the mouth are among the major causes of non-observance of medical treatments, and therefore a lack of success.

To enable fast disintegration, orodispersible tablets have a pore structure and are compressed at pressures lower than conventional tablets, the drawbacks being that they can be more fragile and difficult to handle.

In patent application WO 01/19336, the orodispersible tablets described are obtained by direct compression. However, this direct compression method is not always entirely satisfactory, in particular in terms of friability and disintegration time of the tablets thus obtained.

Patent application WO 00/06126 in the name of Takeda Chemical Industries discloses an ODT form that can contain an active ingredient which is not an opioid, a sugar and between 5 to 7% of hydroxypropylcellulose. The amount of active ingredient is 0.01 and 70 part(s) by weight. The ODT tablets are prepared from coated granules.

Patent application WO 00/78292 in the name of Takeda Chemical Industries discloses an ODT form that can contain morphine in its core and is prepared from mannitol. The amount of active ingredient is between 0.01 and 70 part(s) by weight. The application also discloses the use of micro-crystalline cellulose as a binder, and of crospovidone as a disintegrant.

Patent application WO 2009/086046 filed by Eurand Inc. discloses an ODT form that can contain morphine in its core. The application also discloses povidone or HPC as a binder, crospovidone as a disintegrant, microcrystalline cellulose as a diluent and magnesium stearate as a lubricant.

Patent application WO 2007/141328 in the name of the applicant describes sublingual tablets containing a low dose of active ingredient coated onto a core.

However, at the current time there are still certain characteristics that limit the industrial development of orodispersible tablets, in particular the active ingredient content uniformity for low dosages.

The expression "low dosage of active ingredient" refers to a dosage of from 0.1 to 5%, preferably from 0.2 to 3% and even more preferentially from 0.5 to 1.5% by weight of active ingredient relative to the total weight of the tablet, with an active ingredient content per tablet of from 7 to 0.5 mg, preferably from 5.5 to 1.5 mg, even more preferentially of approximately 5 mg, 2.5 mg or 1 mg.

It therefore currently proves to be necessary to provide an orodispersible tablet containing a low dose of opioid, in particular of morphine or its salts, and which exhibits content uniformity even at low dosage, and a pleasant feeling in the mouth.

SUMMARY

It has now been found, surprisingly, by the applicant that, by means of a very specific formulation, it is possible to industrially obtain orodispersible tablets containing a low dosage of opioid, which exhibit satisfactory content uniformity, a fast disintegration time and an entirely satisfactory acceptability in the mouth.

Thus, a low-dosage orodispersible opioid tablet is provided comprising: to 30%, preferably 15 to 25% and even more preferentially approximately 20% by weight, relative to the total weight of the tablet, of opioid granules, and 70 to 90%, preferably from 75 to 85% and even more preferentially approximately 80% by weight, relative to the total weight of the tablet, of a mixture of compression excipients, the granules comprising 8 to 27%, preferably 10 to 25% by weight, relative to the weight of the granules, of said opioid and 72% to 93%, preferably 70 to 90% by weight, relative to the weight of the granules, of a mixture of diluent and binder, and said mixture of compression excipients comprising at least one disintegrating agent, one soluble diluting agent, one lubricating agent, one permeabilizing agent, and optionally a sweetener, a flavoring and/or a coloring, the ratio between the lubricating agent and the permeabilizing agent being greater than or equal to 1, the amount of lubricating agent being from 1 to 2%, preferably from 1.05 to 1.50% by weight, relative to the total weight of the tablet, and the amount of permeabilizing agent being from 0.5 to 5%, preferably from 1 to 2.5% by weight, relative to the total weight of the tablet.

According to another aspect, a method for preparing an orodispersible tablet is provided.

According to another aspect, the present invention proposes the use of a given amount of magnesium stearate and of a silica having a high affinity for aqueous media, such as a colloidal silica, a precipitated silica, or a mixture of colloidal silica and precipitated silica, preferably a precipitated silica, in order to improve the opioid homogeneity of a low-dosage orodispersible tablet.

DETAILED DESCRIPTION

The present invention relates to a low-dosage orodispersible opioid tablet comprising:

10 to 30%, preferably 15 to 25% and even more preferentially approximately 20% by weight, relative to the total weight of the tablet, of opioid granules, and 70 to 90%, preferably from 75 to 85% and even more preferentially approximately 80% by weight, relative to the total weight of the tablet, of a mixture of compression excipients, the granules comprising 8 to 27%, preferably 10 to 25% by weight, relative to the weight of the granules, of said opioid and 72% to 93%, preferably 70 to 90% by weight, relative to the weight of the granules, of a mixture of diluent and binder, and said mixture of compression excipients comprising at least one disintegrating agent, one soluble diluting agent, one lubricating agent, one permeabilizing agent, and optionally a sweetener, a flavoring and/or a coloring, the ratio between the lubricating agent and the permeabilizing agent being greater than or equal to 1, the amount of lubricating agent being from 1 to 2%, preferably from 1.05 to 1.50% by weight, relative to the total weight of the tablet, and the amount of permeabilizing agent being from 0.5 to 5%, preferably from 1 to 2.5% by weight, relative to the total weight of the tablet.

For the purposes of the present invention, an orodispersible tablet is a tablet which disintegrates or disaggregates in the mouth, only on contact with saliva, without intake of water and without being chewed, in less than 60 seconds, preferably in less than 40 seconds, and even more preferentially in less than 30 seconds, while forming a suspension that is easy to swallow.

The disintegration (or disaggregation) time in the mouth corresponds to the time which separates, on the one hand, the moment at which the tablet is placed in the mouth in contact with the saliva and, on the other hand, the moment at which the suspension resulting from the disintegration (disaggregation) of the tablet in contact with the saliva is swallowed. This disintegration time corresponds to the in vivo disintegration time.

It is also possible to measure the in vitro disintegration time of the orodispersible tablets according to the invention. This disintegration time is measured according to the European Pharmacopeia 2.9.1 on an Erweka ZT 301 device or any other device for measuring the disintegration time of tablets, corresponding to the European Pharmacopeia 2.9.1. The in vitro disintegration time of the tablets according to the invention is from 10 to 20 seconds.

The granules of the present invention relate to agglomerates of particles, which comprise an opioid as active ingredient, a diluent and a binder.

The opioid is chosen from morphine, bupremorphine, desomorphine, dihydromorphine, hydrocodone, hydromorphone, methadone, oxycodone, oxymorphone.

The opioid may be in free form or in the form of an ester, a salt, a hydrate, a solvate, a polymorph, an isomer or other pharmaceutically acceptable forms.

The invention is very particularly suitable for morphine or morphine sulfate. Hereinafter, the term "morphine sulfate" will be used without distinction.

The opioid is present in the granules in a proportion of from 8 to 27%, preferably from 15 to 25% and even more preferentially approximately 20% by weight relative to the total weight of the granules.

The diluent present in the granules is a pharmaceutical acceptable diluent which is soluble and is chosen from mannitol, microcrystalline cellulose, and mixtures thereof.

The binder present in the granules is a pharmaceutically acceptable binder, preferably a cellulose derivative, in particular hydroxypropylcellulose, hydroxypropylmethylcellulose and hydroxyethylcellulose, and mixtures thereof.

The weight ratio between the diluent and the binder in the granules is from 20:1 to 10:1, preferably 15:1.

The granules of the present invention can be obtained by means of a method which is in itself known, such as, for example, extrusion-spheronization, wet granulation or hot granulation.

The granules are present in the orodispersible tablet in a proportion of from to 30%, preferably from 15 to 25%, more preferentially of approximately 20% by weight of the total weight of the tablet. Below 10%, it is difficult to obtain good homogeneity of the active ingredient. Above 30%, the disintegration time of the tablet is decreased and the feeling in the mouth is not very satisfactory.

The orodispersible tablet also comprises a mixture of compression excipients.

A diluting agent present in the mixture of compression excipients is chosen from microcrystalline cellulose, a polyol containing less than 13 carbon atoms, in particular mannitol, xylitol, sorbitol and/or maltitol, or mixtures thereof.

The diluting agent is either in the form of the directly compressible product, the mean particle diameter of which is from 100 to 500 μm, or in the form of a powder, the mean particle diameter of which is less than 100 μm.

At least two different diluting agents, such as mannitol 60 and mannitol SD200, are preferably used.

The proportion of diluting agent selected for constituting the orodispersible tablet, relative to the weight of the tablet, is from 30 to 90% by weight.

The disaggregating agent, also called disintegrating agent or disintegrant, is chosen from the group comprising in particular crosslinked sodium carboxy-methylcellulose denoted in the art by the term croscarmellose, crospovidone, and the mixture thereof. By virtue of the choice and the proportion of this disintegrating agent, the tablet retains a hardness acceptable for normal conditions for handling the tablets when the latter are stored in sealed packaging up to temperatures of at least 30° C.

The proportion of disaggregating agent selected for constituting the orodispersible tablet is from 1 to 15% by weight, preferably from 2 to 10% by weight and more preferentially approximately 5% by weight, relative to the weight of the tablet.

The lubricant preferentially used in this mixture of excipients is chosen from the group comprising magnesium stearate, sodium stearyl fumarate, stearic acid, micronized polyethylene glycol (micronized Macrogol 6000), and mixtures thereof. It can be used in a proportion of from 1 to 2% by weight relative to the total weight of the tablet. Magnesium stearate is preferably used. An amount of less than 1% may be insufficient in industrial conditions, in particular for low dosages, and may cause sticking. An amount greater than 2% increases the disintegration time of the tablet.

As permeabilizing agent, use is made of a tablet chosen from the group comprising in particular silicas having a high affinity for aqueous solvents, such as colloidal silicas, precipitated silicas, for example precipitated silicas known under the trademark Syloid®, maltodextrins, β-cyclodextrins, and mixtures thereof.

According to one advantageous embodiment of the tablets in accordance with the invention, the permeabilizing agent is chosen from precipitated silica, colloidal silica, and mixtures thereof, and even more advantageously the permeabilizing agent is a precipitated silica. This is because, not only do these silicas contribute to better disaggregation of the tablets, but in addition, by virtue of their permeabilizing/flow agent properties, they promote particular rearrangements during compression and they make it possible, on the one hand, to reduce the amount of hydrophobic lubricant required to ensure production under optimal conditions and, on the other hand, to reduce the strength of the compression force so as to obtain a tablet that can be handled under industrial conditions.

The proportion of permeabilizing agent relative to the weight of the tablet is between 0.5 and 5% by weight, preferably from 1 to 2.5% by weight, relative to the total weight of the tablet.

In order to obtain good homogeneity of the active ingredient and a satisfactory disintegration time without difficulty during industrial production, it is important for the weight ratio of the lubricant to the permeabilizing agent to be greater than or equal to 1.

The mixture of excipients which goes into the composition of the tablets according to the invention can also comprise a sweetener, a flavoring and a coloring.

The sweetener may be chosen from the group comprising in particular aspartame, potassium acesulfame, sodium saccharinate, neohesperidin dihydrochal-cone, and mixtures thereof.

The flavorings and colorings are those normally used in the pharmaceutical industry for the preparation of tablets.

The tablets in accordance with the invention show, compared to the tablets of the type in question that already exist, an improvement in palatability and in particular taste and texture, and can make it possible to reduce the tablet/active ingredient dose weight ratio.

They have a satisfactory hardness which allows them to be handled under standard operating conditions without particular operating precautions. By way of indication, it is pointed out that hardnesses corresponding to these conditions are generally between 20 and 70 newtons.

According to one particular embodiment, the tablet according to the invention comprises:

10 to 30% of opioid granules;
60 to 85% of diluent;
2 to 10% of disintegrant;
1 to 2% of lubricant;
0.5 to 5% of permeabilizing agent;
0 to 5% of sweetener, of flavoring and/or of coloring,
the percentages being by weight relative to the total weight of the tablet.

The invention also relates to a method for preparing an orodispersible tablet as described above, comprising:

preparation of opioid granules by wet granulation, dry granulation, hot granulation and/or spheronization of said opioid with a diluent and a binder;
preparation of a pulverulent mixture comprising a disintegrant, a diluent, a permeabilizing agent and optionally a flavoring, a sweetener and/or a coloring;
mixing of the opioid granules with the pulverulent mixture obtained in the preceding step;
lubrication of the mixture by adding the lubricating agent;
compression of the lubricated mixture.

The granules are prepared in the following way:

A step of mixing the active ingredient, the diluent and the binder is carried out at a paddle speed of between 200 and 80 rpm (rotations per minute), preferably between 170 and 110 rpm and even more preferentially of 140 rpm, at a temperature of between 30 and 10° C., preferably between 25 and 15° C., and even more preferentially at 20° C. The duration of this step is between 500 and 75 seconds, preferably between 400 and 150 seconds and even more preferentially of 300 seconds, so as to obtain a homogeneous mixture.

A wetting step is then carried out according to the general knowledge of those skilled in the art, as a function of the amount of starting material used.

Finally, a granulation step is carried out at a paddle speed of between 170 and 50 rpm (rotations per minute), preferably between 140 and 80 rpm and even more preferentially of 110 rpm, at a temperature of between 30 and 10° C., preferably between 25 and 15° C. and even more preferentially at 20° C.; the lump breaker speed being between 1500 and 500 rpm, preferably between 1250 and 750 rpm, and even more preferentially at 1000 rpm.

The grains obtained by granulation are dried up to a temperature of between 40 and 24° C., preferably between 36 and 28° C., and even more preferentially at 32° C. The drying is continued until a loss on drying of less than 3.00% is reached. This loss on drying is performed by means of a Mettler HR 73 thermobalance (10 minutes at 105° C.).

A step of reducing the particle size is then carried out by means of a mill (knife/hammer mill or conical mill), followed by sieving through a grill having an opening of 1100 μm to 100 μm, preferably between 800 μm and 200 μm and even more preferentially 500 μm.

The mixture of compression excipients, with the exception of the lubricant, is prepared separately.

The previously prepared granules are then added.

It is also possible to mix the granules with a part of the compression excipients and then to add the remaining excipients.

The lubrication step is carried out in the following way.

The total amount of lubricant, preferably magnesium stearate, is added to the mixture previously prepared, and the lubrication is carried out with a rotation speed of between 1 and 20 rpm, preferably between 5 and 15 rpm and even more preferentially 10 rpm, for 1 to 12 minutes, preferably 3 to 9 minutes and even more preferentially 6 minutes depending on the weight of the mixture.

The compression step is carried out on a rotary machine which is set so as to obtain tablets having the given target weight and hardness characteristics.

Finally, the invention relates to the use of 1 to 2% of lubricant and of a permeabilizing agent in a lubricant/permeabilizing agent ratio >1, in order to improve the opioid active ingredient homogeneity of a low-dosage orodispersible tablet, the % being by weight relative to the weight of the orodispersible tablet.

The examples hereinafter make it possible to understand the invention more clearly. They are given only by way of illustration but are not limiting.

EXAMPLES

Example 1

Orodispersible tablets of morphine sulfate containing doses of 1 mg, 2.5 mg and 5 mg are prepared.

These tablets are prepared as indicated hereinafter, with the constituents presented in table 1 below.

Lubrication Step:

The total amount of magnesium stearate is added to the mixture previously produced; the lubrication is carried out with a rotation speed of 10 rpm for 6 minutes.

The mixture obtained is compressed on a rotary machine in order to obtain tablets having the target weight and hardness characteristics given in tables 2 to 4 respectively for the morphine tablets containing a dose of 1 mg, 2.5 mg and 5 mg.

TABLE 1

| Ingredient | Function | % | Dosage 1 mg | Dosage 2.5 mg | % | Dosage 5 mg | % |
|---|---|---|---|---|---|---|---|
| For the granules | | | | | | | |
| Morphine sulfate | Active ingredient | 2.00% | 1.0 mg | 2.5 mg | 2.0% | 5.0 mg | 2.00% |
| Mannitol 60 | Diluent | 7.50% | 3.8 mg | 9.4 mg | 7.50% | 18.75 mg | 7.50% |
| Hydroxypropylcellulose | Binder | 0.50% | 0.3 mg | 0.6 mg | 0.50% | 1.25 mg | 0.50% |
| Compression excipients | | | | | | | |
| Crospovidone (Polyplasdone Ultra ®) | Disintegrant | 5.00% | 2.5 mg | 6.3 mg | 5.00% | 12.5 mg | 5.00% |
| Mannitol SD200 | Diluent | 55.80% | 27.9 mg | 69.8 mg | 55.80% | 139.5 mg | 55.80% |
| Mannitol 60 | Diluent | 13.95% | 7.0 mg | 17.4 mg | 13.95% | 34.9 mg | 13.95% |
| Microcrystalline cellulose | Diluent | 10.00% | 5.0 mg | 12.5 mg | 10.00% | 25.0 mg | 10.00% |
| Acesulfame K + | Sweetener | 2.00% | 1.0 mg | 2.5 mg | 2.00% | 5.0 mg | 2.00% |
| Orange flavor | Flavoring | 1.00% | 0.5 mg | 1.3 mg | 1.00% | 2.5 mg | 1.00% |
| Precipitated Silica (Syloid 244 ®) | Flow/permeabilizing agent | 1.00% | 0.5 mg | 1.3 mg | 1.00% | 2.5 mg | 1.00% |
| Magnesium Stearate | Lubricant | 1.25% | 0.6 mg | 1.6 mg | 1.25% | 3.1 mg | 1.25% |
| | TOTAL | 100.0% | 50 mg | 125 mg | 100.0% | 250 mg | 100.0% |

A step of mixing the following starting materials is carried out: HPC-SL, mannitol 60 PhE, morphine sulfate, at a paddle speed of 140 rpm at a temperature of approximately 20° C.

The duration of this step is 300 seconds so as to obtain a homogeneous mixture.

A step of wetting the above mixture by means of a peristatic pump is carried out. The duration of this step is from 1 to 10 minutes, preferably 2 to 5 minutes and even more preferentially 3 minutes.

Finally, the granulation is carried out at a paddle speed of 110 rpm and at a temperature of 20° C.; the lump breaker speed is 1000 rpm.

The duration of the granulation step is approximately 60 seconds.

The grains obtained are dried at a temperature of 32° C. The drying is continued until a loss on drying of less than 3.00% is reached.

The granules then undergo a size reduction step by means of a mill through a grill having an opening of 500 μm.

Premixing and mixing of the external phase are then carried out.

The following materials are premixed in a container: morphine sulfate granules obtained previously, polyplasdone ultra, potassium acesulfame, flavoring, Syloid 244, half the total amount of mannitol 200 SD.

The speed of rotation of the container is set at 10 rpm for 1 to 2 minutes, preferably 5 to 15 minutes and even more preferentially 10 minutes.

The step of mixing with addition of the second half of the mannitol 200 SD, the mannitol 60 and the microcrystalline cellulose then follows at a container rotation speed of 10 rpm for 30 minutes.

TABLE 4

| Parameter | Target |
|---|---|
| Weight | 50 mg |
| Hardness | 40N |

TABLE 5

| Parameter | Target |
|---|---|
| Weight | 125 mg |
| Hardness | 55N |

TABLE 6

| Parameter | Target |
|---|---|
| Weight | 250 mg |
| Hardness | 60N |

For each of the tablets, the average time for disaggregation in the mouth was 40 seconds.

Example 2

The procedure was carried out as for example 1, with the compositions given in table 7 below.

TABLE 7

| Ingredient | Function | % | Dosage 1 mg | Dosage 2.5 mg | % | Dosage 5 mg | % |
|---|---|---|---|---|---|---|---|
| | | For the granules | | | | | |
| Morphine sulfate | API | 2.00% | 1.0 mg | 2.5 mg | 2.00% | 5.0 mg | 2.00% |
| Mannitol 60 | Diluent | 7.50% | 3.8 mg | 9.4 mg | 7.50% | 18.75 mg | 7.50% |
| Hydroxypropylcellulose | Binder | 0.50% | 0.3 mg | 0.6 mg | 0.50% | 1.25 mg | 0.50% |
| | | Mixture of compression excipients | | | | | |
| Crospovidone (Polyplasdone Ultra ®) | Disintegrant | 5.00% | 2.5 mg | 6.3 mg | 5.00% | 12.50 mg | 5.00% |
| Mannitol SD200 | Diluent | 56.00% | 28.0 mg | 70.0 mg | 56.00% | 140.0 mg | 56.00% |
| Mannitol 60 | Diluent | 14.00% | 7.0 mg | 17.5 mg | 14.00% | 35.0 mg | 14.00% |
| Microcrystalline cellulose | Diluent | 10.00% | 5.0 mg | 12.5 mg | 10.00% | 25.0 mg | 10.00% |
| Acesulfame K + | Sweetener | 2.00% | 1.0 mg | 2.5 mg | 2.00% | 5.0 mg | 2.00% |
| Orange flavor | Flavoring | 1.00% | 0.5 mg | 1.3 mg | 1.00% | 2.5 mg | 1.00% |
| Syloid | Flow/permeabilizing agent | 1.00% | 0.5 mg | 1.3 mg | 1.00% | 2.5 mg | 1.00% |
| Magnesium Stearate | Lubricant | 1.00% | 0.5 mg | 1.3 mg | 1.00% | 2.5 mg | 1.00% |
| | TOTAL | 100.00% | 50 mg | 125 mg | 100.00% | 250 mg | 100.00% |

For the tablet at 1%, a slight sticking during compression was observed.

Example 3

The procedure was carried out as in example 1 with the following compositions

TABLE 8

| Ingredient | Function | % | Dosage 1 mg | Dosage 2.5 mg | % | Dosage 5 mg | % |
|---|---|---|---|---|---|---|---|
| | | For the granules | | | | | |
| Morphine sulfate | API | 2.00% | 1.0 mg | 2.5 mg | 2.00% | 5.0 mg | 2.00% |
| Mannitol 60 | Diluent | 7.50% | 3.8 mg | 9.4 mg | 7.50% | 18.75 mg | 7.5% |
| Hydroxypropylcellulose | Binder | 0.50% | 0.3 mg | 0.6 mg | 0.50% | 1.25 mg | 0.50% |
| | | Mixture of compression excipients | | | | | |
| Crospovidone | Disintegrant | 5.00% | 2.5 mg | 6.3 mg | 5.00% | 12.50 mg | 5.00% |
| Mannitol SD200 | Diluent | 55.60% | 27.8 mg | 69.5 mg | 55.60% | 139.0 mg | 55.60% |
| Mannitol 60 | Diluent | 13.90% | 7.0 mg | 17.4 mg | 13.90% | 34.8 mg | 13.90% |
| Microcrystalline cellulose | Diluent | 10.00% | 5.0 mg | 12.5 mg | 10.00% | 25.0 mg | 10.00% |
| Acesulfame K + | Sweetener | 2.00% | 1.0 mg | 2.5 mg | 2.00% | 5.0 mg | 2.00% |
| Orange flavor | Flavoring | 1.00% | 0.5 mg | 1.3 mg | 1.00% | 2.5 mg | 1.00% |
| Syloid | Flow/permeabilizing agent | 1.00% | 0.5 mg | 1.3 mg | 1.00% | 2.5 mg | 1.00% |
| Magnesium Stearate | Lubricant | 1.50% | 0.8 mg | 1.9 mg | 1.50% | 3.75 mg | 1.50% |
| | TOTAL | 100.00% | 50 mg | 125 mg | 100.00% | 250 mg | 100.00% |

No difficulty was apparent during the production of these tablets. They exhibited a disintegration time in the mouth of less than 40 seconds and were entirely satisfactory in the mouth.

The invention claimed is:

1. A low-dosage orodispersible opioid tablet comprising:

10 to 30% by weight, relative to the total weight of the tablet, of opioid granules, said granules having a particle size from 200 to 1,100 µm, said granules consisting of:

7 to 28% by weight, relative to the weight of the granules, of an opioid selected from morphine or morphine sulfate as an active ingredient, and 72% to 93% by weight, relative to the weight of the granules, of a mixture of diluent and binder, said diluent being selected from the group consisting of mannitol, microcrystalline cellulose, and mixtures thereof, and said binder being selected from the group consisting of hydroxypropylcellulose, hydroxypropylmethylcellulose, hydroxyethylcellulose and mixtures thereof, wherein a ratio between the diluent and the binder in said granules is from 20:1 to 10:1, and 70% to 90% by weight, relative to the total weight of the tablet, of a mixture of compression excipients consisting of at least one disintegrating agent, one diluting agent, one lubricating agent, one permeabilizing agent, and optionally a sweetener, a flavoring agent, and/or a coloring agent, wherein:

a ratio between the lubricating agent and the permeabilizing agent being greater than 1, the lubricating agent is present in an amount from 1 to 2% by weight, relative to the total weight of the tablet, and the permeabilizing agent is present in an amount from 0.5 to less than 2% by weight, relative to the total weight of the tablet, wherein said opioid is the active ingredient of the low-dosage orodispersible opioid tablet.

2. The orodispersible tablet as claimed in claim 1, comprising:

10 to 30% of opioid granules;

60 to 85% of diluting agent;

2 to 10% of disintegrating agent;

1 to 2% of lubricating agent;

0.5 to less than 2% of permeabilizing agent; and 0 to 5% of sweetener, of flavoring agent and/or of coloring agent, the percentages being by weight relative to the total weight of the tablet.

3. The orodispersible tablet as claimed in claim 1, wherein the diluting agent is selected from the group consisting of microcrystalline cellulose, at least one polyol containing less than 13 carbon atoms, and mixtures thereof.

4. The orodispersible tablet as claimed in claim 1, wherein the disintegrating agent is selected from the group consisting of: crospovidone, croscarmellose, and mixtures thereof.

5. The orodispersible tablet as claimed in claim 1, wherein the lubricating agent is selected from the group consisting of magnesium stearate, sodium stearyl fumarate, stearic acid, micronized polyethylene glycol, and mixtures thereof.

6. The orodispersible tablet as claimed in claim 1, wherein the permeabilizing agent is selected from the group consisting of precipitated silica, colloidal silica, maltodextrin, beta-cyclodextrin, and mixtures thereof.

7. The orodispersible tablet as claimed in claim 1, wherein the orodispersible tablet comprises:

10 to 30% of morphine or morphine sulfate granules;

60 to 85% of a mixture of mannitol and microcrystalline cellulose as diluting agent;

2 to 10% of crospovidone as disintegrating agent;

1 to 2% of magnesium stearate as lubricating agent;

0.5 to less than 2% of permeabilizing agent selected from the group consisting of precipitated silica, colloidal silica, and mixtures thereof; and 0 to 5% of sweetener, of flavoring agent and/or of coloring agent, the percentages being by weight relative to the total weight of the tablet.

8. A method for preparing an orodispersible tablet as defined in claim 1, comprising:

preparing opioid granules by wet granulation, dry granulation, hot granulation and/or spheronization of said opioid with a diluent and a binder, the ratio between the diluent and the binder in said granules is from 20:1 to 10:1, and reducing particle size of the granules using a mill followed by sieving through a grill having an opening of 1,100 μm to 200 μm to obtain prepared opioid granules;

preparing a pulverulent mixture comprising a disintegrating agent, a diluting agent, a permeabilizing agent and optionally a flavoring agent, a sweetener, and/or a coloring agent;

mixing of the prepared opioid granules with the prepared pulverulent mixture obtained in the preceding steps;

lubricating the mixture of the prepared opioid granules with the prepared pulverulent mixture by adding the lubricating agent, the ratio between the lubricating agent and the permeabilizing agent (which is present in the prepared pulverulent mixture) being greater than 1; and compressing the lubricated mixture.

9. The orodispersible tablet as claimed in claim 1, wherein the diluting agent in the mixture of compression excipients is selected from the group consisting of:

microcrystalline cellulose, a polyol selected from the group consisting of mannitol, xylitol, sorbitol, maltitol, and mixtures thereof, and mixtures thereof.

10. The orodispersible tablet as claimed in claim 7, wherein the permeabilizing agent is precipitated silica.

* * * * *